W. H. HORNUM.

Assignor, by mesne assignments, to THE HORNUM PATENT REGISTER MANUFACTURING COMPANY.

Fare Registers.

No. 8,014. Reissued Dec. 25, 1877.

Witnesses.

Otto Hufeland

Chas. Kahlers.

Inventor.

William Hans Hornum by

Van Santvoord & Hauff his attorneys.

N. PETERS, PHOTO-LITHOGRAPHER, WASHINGTON, D. C.

UNITED STATES PATENT OFFICE.

WILLIAM H. HORNUM, OF NEW YORK, N. Y., ASSIGNOR, BY MESNE ASSIGNMENTS, TO THE HORNUM PATENT REGISTER MANUFACTURING COMPANY.

IMPROVEMENT IN FARE-REGISTERS.

Specification forming part of Letters Patent No. 171,133, dated December 14, 1875; Reissue No. 8,014, dated December 25, 1877; application filed November 30, 1877.

*To all whom it may concern:*

Be it known that I, WILLIAM H. HORNUM, of the city, county, and State of New York, have invented a new and useful Improvement in Fare-Registers, which improvement is fully set forth in the following specification, reference being had to the accompanying drawing, in which—

Figure 1:
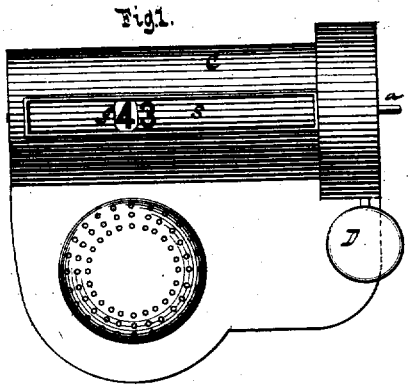
Figure 2:
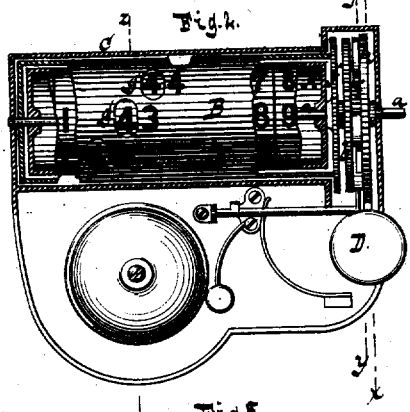
Figure 3:
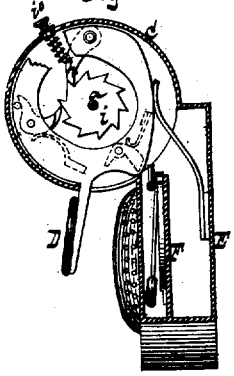
Figure 4:
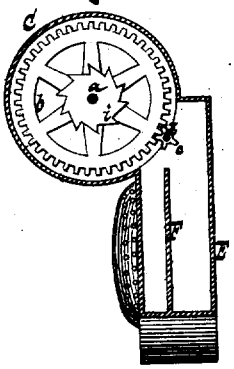
Figure 5:
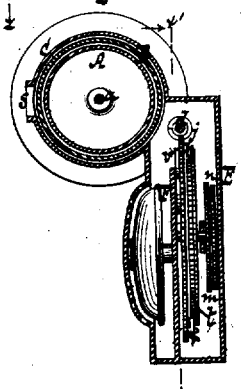
Figure 6:
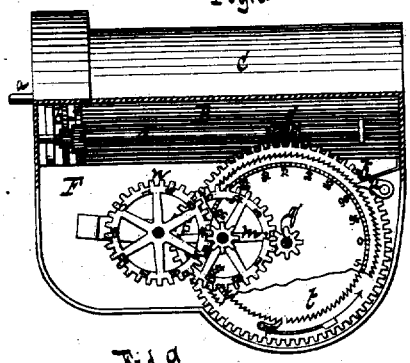
Figure 7:
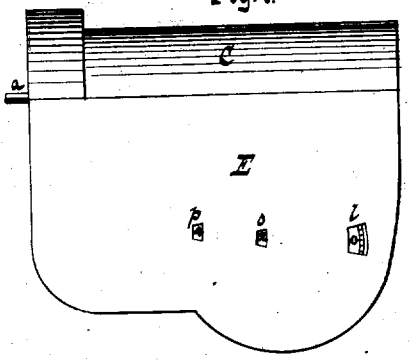
Figure 9:
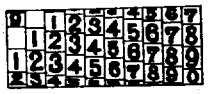
Figure 8:
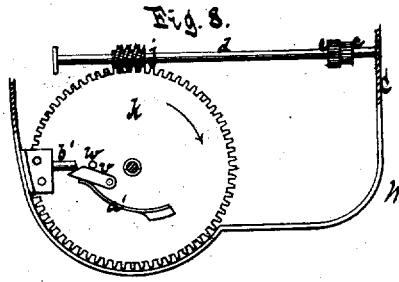

Figure 1 represents a face view of the apparatus complete. Fig. 2 is a similar view, partly in section. Fig. 3 is a transverse section in the plane *x x*, Fig, 2. Fig. 4 is a similar section in the plane *y y*, Fig. 2. Fig. 5 is a similar section in the plane *z z*, Fig. 2. Fig. 6 is a face view, showing the supplemental general register. Fig. 7 is a back view. Fig. 8 is a section in the plane *x′ x′*, Fig. 5, looking in the direction of the arrow opposite to that line. Fig. 9 is a detached view of the inner cylinder, forming part of the registering mechanism.

Similar letters indicate corresponding parts.

This invention consists in the combination of two cylinders—one working inside the other—said cylinders being made to revolve step by step, both in the same direction, but with different velocities, in the interior of a case provided with a rectilinear slot, the surface of the inner cylinder being divided off into one hundred spaces, forming ten rows of ten spaces each, which extend, in slightly oblique directions, from end to end of said cylinder, and nine of which contain the figures from 1 to 9, one space in each row being left blank, while the outer cylinder is marked with the figures from 0 to 9, arranged in a spiral line extending all round the surface of said cylinder on the sides of openings, also arranged in a spiral running parallel with the spiral of the figures, so that by imparting to the two cylinders a step-by-step motion, as above stated, the figures from 0 to 99 are successively brought opposite the slot in the external case.

The invention consists, also, in the combination, in a fare-register, of a single-trip register composed of two cylinders—one working inside the other—an actuating mechanism for imparting to the two cylinders a step-by-step motion, and a case inclosing the two cylinders, with a general register, which is geared together with the single-trip register by cog-wheels and a worm, so that the two registering devices are compelled to work together without fail, and the general register serves to control the single-trip register.

The invention consists, further, in the combination, in a fare-register, of a general register, a single-trip register, a ratchet-wheel and pawl, which transmit motion to the general register every time when the single-trip register is moved forward but not when the same is moved back, and a yielding zero-stop, so that both registering mechanisms can be moved forward without any obstruction, but when the single-trip register is moved backward its motion is arrested by the zero-stop, while such backward motion does not affect the general register; also, in the combination, in a fare-register, of a general register, a single-trip register, actuating mechanism common to both, and a yielding zero-stop, the single-trip register being adapted to be moved back independent of the actuating mechanism and of the general register, so that by the operation of the actuating mechanism both registers can be moved forward to any desired point, but in moving the single-trip register back its motion is arrested at zero, while the general register remains stationary during the backward motion of the single-trip register.

In the drawings, the letters A B designate two cylinders, which work, one inside the other, in the interior of a case, C, which is provided with a rectilinear slot, *s*, extending nearly through its whole length. (See Fig. 1.) The inner cylinder A is firmly mounted on an arbor, *a*, which has its bearings in the heads of the case C, and on which the outer cylinder B revolves loosely.

On the shaft *a* is firmly secured a cog-wheel, *b*, which gears in a pinion, *c*, Fig. 6, mounted on a shaft, *d*, on which is fastened a second pinion, *e*, which gears in a cog-wheel, *f*, secured to the end of the outer cylinder B, the proportion between the cog-wheels *b f* and pinions *c e* being such that when the inner cylinder is turned the outer cylinder is caused to move at a different speed from that of the inner one.

The surface of the inner cylinder is divided off in one hundred spaces, arranged in ten rows, which extend in slightly oblique directions from one end of the cylinder to the other, or nearly so. Each row contains ten spaces, and the figures from 1 to 9, one space in each row being left blank. (See Fig. 9.) The outer cylinder is marked with the figures from 0 to 9, which are arranged on a spiral line extending all around said cylinder on the sides of the openings *g*, Fig. 3, which are also arranged on a spiral line running parallel to the line of the figures.

It will be readily seen from this description that the two cylinders can be turned to such a position that one of the blank spaces of the inner cylinder comes under the opening alongside the 0 on the outer cylinder, and in line with the slot *s* in the case. If the inner cylinder is then turned so as to bring successively its blank spaces in line with the slot *s*, while the outer cylinder is turned to bring successively the figures 1, 2, 3, &c., in line with said slot, the apparatus will indicate the figures 0 to 9. As the motion continues, the spaces of the inner cylinder containing the figures 1 to 9 on the outer cylinder come in line with said slot, and the apparatus indicates the numbers 10 to 19, and so on.

It is obvious that the motion of the two cylinders can be easily regulated by the cog-wheels *b f* and pinions *c e*, so as to produce the desired result, according to the manner in which the figures are placed on the inner and outer cylinders, which may be changed in various ways.

In the example shown in the drawing, the motion of the inner cylinder is produced by a finger-lever, D, which carries a pawl, *h*, that engages with a ratchet-wheel, *i*, secured to the cog-wheel *b*.

On the shaft *d* is mounted a worm, *j*, Figs. 6 and 8, which engages with a cog-wheel, *k*, situated close to the partition-plate F of the case inclosing the working parts of my apparatus. (See Fig. 5.) On the under side of this cog-wheel, or on a disk secured on its arbor, are one hundred marks, which show through an aperture, *l*, in the back plate E, Fig. 7, and said wheel is geared together with additional registering-wheels *m n*, marked with figures, which show through apertures *o p* in the back plate. By these means a continuous or general registering mechanism is connected with two cylinders, A B, to register hundreds, thousands, ten thousands, and so on.

The cog-wheel *k* is mounted loosely on its shaft *q*, and is connected to the same by a pawl, *r*, and ratchet-wheel *t*, Fig. 6, said ratchet-wheel being firmly mounted on the shaft. A stop-pawl, *u*, prevents this ratchet-wheel from being turned in the wrong direction.

The shaft *a* of the two registering-cylinders A B extends through the case C, and is provided with a square for the reception of a key, which serves to return the cylinders A B to zero at the end of each trip. These cylinders therefore form the single-trip register, while the wheels *k m n* form the general register.

In order to be able to set the single-trip register back to zero, the moving-pawl *h* of the finger-lever D can be thrown out of gear with the ratchet-wheel *i* by a finger-piece, $i^{o}$, Fig. 3. While the single-trip register is being turned back, the wheel *k*, which transmits motion to the general register, turns in a direction opposite to the arrow marked on it in Figs. 6 and 8, and the general register remains stationary.

In order to guard against defraudations, however, it is requisite that the single-trip register, in being turned back, shall be arrested at zero, for unless this is the case the conductor is enabled to manipulate his single-trip register without moving the general register to suit his own fraudulent purposes. For instance, at the beginning of his trip, the conductor turns his single-trip register back until it indicates any desired number—for instance, eight. At the time of entering the car he finds twenty passengers and he registers twelve, so that the figures exposed on the single-trip register tally with the number of passengers in the car. During the remainder of the trip he takes twenty more fares, which are all registered, the single-trip register showing the number 40, while the general register has been propelled only thirty-two steps. To make both registers tally, the conductor turns the single-trip register back eight figures, and he pockets eight fares.

Such frauds are effectually prevented by the zero-stop *v*, which is pivoted to the wheel *k*, (see Fig. 8,) and held up against a pin, *w*, by a spring, *a'*. The face of the zero-stop is inclined, so that when the wheel *k* is turned forward in the direction of the arrow marked thereon in Fig. 8, said stop, in coming in contact with a fixed pin, *b'*, will yield, and consequently the forward motion of said wheel and of the entire registering mechanism is not interfered with; but if the single-trip register is turned back, the wheel *k* turns in a direction opposite to the arrow marked on it in Fig. 8 until the zero-stop *v* strikes the fixed pin *b'*, which is so situated that it arrests the single-trip register at zero.

This yielding zero-stop is applicable to registering mechanism of various construction, and its advantage over a rigid zero-stop is, that the former allows of turning the registering mechanism forward to any desired point, while the latter arrests the registering mechanism when the same is turned forward as well as when it is turned back. If the capacity of the single-trip register is 100, no more than this number can be registered with the rigid zero-stop; but with the yielding zero-stop there is no limit, since every time the single-trip register is moved forward one step, the general register is also moved, and, consequently, if the single-trip register is turned beyond 100, so that it shows 18 or any other number, the general register will at once expose the correct number.

I do not claim in this application for a patent a rigid zero-stop in combination with the mechanism of a fare-register, such being shown and claimed in my Patent No. 165,832; Reissue No. 7,554.

What I claim as new, and desire to secure by Letters Patent, is—

1. In a registering apparatus, the combination of two cylinders, one working inside the other, and geared together to move at different velocities in a case, C, having a slot, *s*, the inner cylinder A being divided off in a series of spaces containing figures from 0 to 9, arranged on a spiral line alongside of apertures *g*, all constructed and operating substantially as shown and described.

2. The combination, in a registering apparatus, of two cylinders, A B, one working inside the other, with the supplemental or general mechanism composed of a worm, *j*, and wheels *k m n*, substantially as set forth.

3. The combination, in a fare-register, of a general register, a single-trip register, a ratchet-wheel and pawl, which transmit motion to the general register every time when the single-trip register is moved forward, but not when the same is moved back, and a yielding zero-stop, whereby both registering mechanisms can be moved forward without obstruction, but when the single-trip register is moved backward its motion is arrested at zero, while during said backward motion the general register remains stationary, substantially as set forth.

4. The combination, in a fare-register, of a general register, a single-trip register, actuating mechanism common to both, and a yielding zero-stop, the single-trip register being adapted to be moved back independent of the actuating mechanism and of the general register, substantially as and for the purpose shown and described.

In testimony that I claim the foregoing I have hereunto set my hand and seal this 26th day of November, 1877.

WILLIAM H. HORNUM. [L. S.]

Witnesses:

W. HAUFF,

E. F. KASTENHUBER.